PLT-172 SR
C5203 OR PP 003,453

Jan. 29, 1974 J. G. HANNAFORD Plant Pat. 3,453
APPLE TREE
Filed March 1, 1972

SPUR ORIGINAL TREE

SPURTYPE LIMB ORIGINAL TREE

FRUIT ORIGINAL TREE

United States Patent Office

Plant Pat. 3,453
Patented Jan. 29, 1974

3,453
APPLE TREE

John Gould Hannaford, Mount Bera, Cudlee Creek, South Australia, Australia, assignor to Granny Spur Enterprises, Orondo, Wash.

Filed Mar. 1, 1972, Ser. No. 231,034
Int. Cl. A01h 5/03
U.S. Cl. Plt.—34 1 Claim

ABSTRACT OF THE DISCLOSURE

Originating as a genetic bud sport on a standard Granny Smith apple tree in the present discoverer's orchard at Mount Bera, Cudlee Creek, South Australia, this new Granny Smith mutation exhibits vigorous spur-type growth with foliage that is deep green and dense and fruit that is deeper green than that of the parent.

This invention or discovery relates to a new and distinct variety of Granny Smith apple tree which originated from one bud of a multiple subsectioned fruit spur on a standard Granny Smith tree growing in the discoverer's orchard at Mount Bera, Cudlee Creek, South Australia. In the original discovery the port limb, which appeared to be some sixteen years old growing on a mature standard Granny Smith tree, carried a full crop of fruit while the standard tree itself was in an "off crop" condition.

The limb sport representing this new and distinct spur-type variety, and successive generations reproduced therefrom, exhibit all of the characteristics of a true spur-type tree. The limb and its progeny carried a predominance of vigorous, robust spurs, short laterals with short internodes and prominant auxiliary buds. The foliage is deep green and dense, and in contrast to fruit on the standard Granny Smith parent tree, the fruit on this novel mutation is colored deep green and the stems deeper green than normal. The leaves have approximately 25 percent more chlorophyll and are thinner and denser than the leaves of the parent standard Granny Smith tree. Early growth is vigorous.

In terms of size, the fruit of the mutation is large. Moreover, it stores at least as well as long as that of the standard tree.

The discoverer has caused asexual reproduction of the new variety by means of budding, and has found the outstanding characteristics of the new variety to be permanent and stable.

TREE

Figure 1:
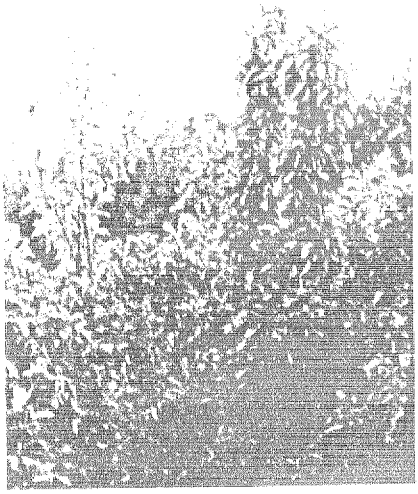
FIG. 1 is a photograph of the new original spur limb structure, fully leaved, growing in the top of its parent standard Granny Smith tree.
Figure 2:
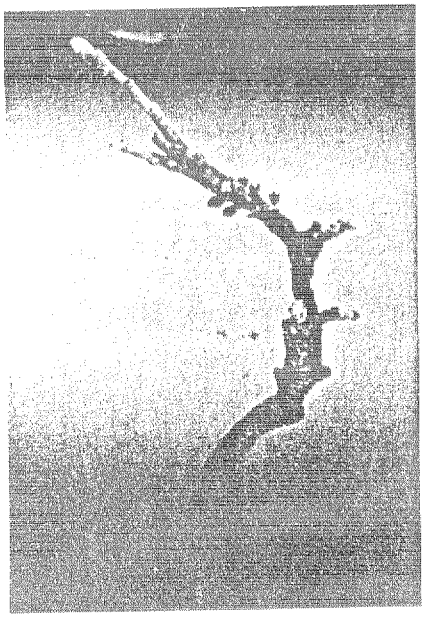
FIG. 2 is a photograph of the original spur limb of the new variety in bud.
Figure 3:
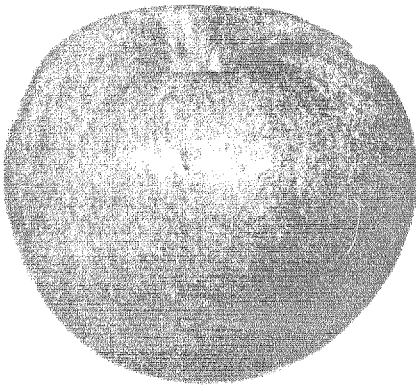
FIG. 3 is a photograph of an apple produced by the original spur limb on the parent tree.

Medium small, semi-dwarf, vigorous growth and compact form. Exhibits the characteristics of growth, size, shape, foliation and fruiting of spur-type trees generally. It exhibits a predominance of vigorous, robust spurs, short laterals with short internodes and prominant auxiliary buds, as compared with the parent standard Granny Smith tree.

FLOWERS AND LEAVES

The flowers are substantially identical with those of the standard Grany Smith tree. The leaves are dark or deep green and dense in contrast with those of the standard Granny Smith tree. They have approximately 25 percent more chlorophyll and are thinner than those of the standard tree.

FRUIT

Generally large, attractive and darker green in comparison with fruit of the standard tree.

I claim:

1. A new and distinct variety of Granny Smith apple tree characterized as to novelty primarily by the spur-type form and growth characteristics including the predominance of vigorous, robust spurs, short laterals with short internodes and prominant auxiliary buds, foliage which is deeper green and denser, having approximately 25 percent more chlorophyll and thinner than the standard tree leaves, and finally by fruit which is deeper green and with stems deeper green than fruit of the standard tree.

No references cited.

R. E. BAGWILL, Primary Examiner